US 8,010,188 B2

(12) United States Patent
Tateno

(10) Patent No.: US 8,010,188 B2
(45) Date of Patent: Aug. 30, 2011

(54) DRUG INJECTING DEVICE

(75) Inventor: Hiroto Tateno, Kagoshima (JP)

(73) Assignee: Kagoshima University, Kagoshima-shi (JP)

( * ) Notice: Subject to any disclaimer, the term of this patent is extended or adjusted under 35 U.S.C. 154(b) by 172 days.

(21) Appl. No.: 12/514,950

(22) PCT Filed: Nov. 13, 2007

(86) PCT No.: PCT/JP2007/071954
§ 371 (c)(1),
(2), (4) Date: May 14, 2009

(87) PCT Pub. No.: WO2008/059810
PCT Pub. Date: May 22, 2008

(65) Prior Publication Data
US 2010/0049118 A1    Feb. 25, 2010

(30) Foreign Application Priority Data
Nov. 14, 2006  (JP) .................................. 2006-308270

(51) Int. Cl.
*A61N 1/30*   (2006.01)
*A61M 31/00*  (2006.01)
*A61B 5/05*   (2006.01)
*A61B 5/00*   (2006.01)

(52) U.S. Cl. ........... 604/20; 600/347; 600/365; 604/504

(58) Field of Classification Search ..................... 604/20, 604/21, 504; 128/200.16; 601/2; 600/347, 600/365
See application file for complete search history.

(56) References Cited

U.S. PATENT DOCUMENTS

| 3,196,384 | A | * | 7/1965 | Dumke et al. | 330/5.5 |
| 3,234,482 | A | * | 2/1966 | Rowen et al. | 330/5.5 |
| 3,325,748 | A | * | 6/1967 | Crabbe | 331/107 A |
| 3,990,452 | A | * | 11/1976 | Murry et al. | 606/169 |
| 4,195,244 | A | * | 3/1980 | Heyman | 310/311 |
| 4,767,402 | A |   | 8/1988 | Kost et al. | |
| 5,135,480 | A |   | 8/1992 | Bannon et al. | |

(Continued)

FOREIGN PATENT DOCUMENTS

JP           63-29662 A    2/1988
(Continued)

OTHER PUBLICATIONS

Townsend et al., Modelling of particle paths passing through an ultrasonic standing wave, 2004, Ultrasonics 42, 319-324.*

*Primary Examiner* — Theodore Stigell
*Assistant Examiner* — William Carpenter
(74) *Attorney, Agent, or Firm* — Arent Fox, LLP

(57) ABSTRACT

There is provided a drug injecting device including a drug feeding unit (110) feeding a drug (111a) to a surface of an object (200), an ultrasonic oscillating unit (120) oscillating an amplitude-modulated ultrasonic wave group in which amplitudes of respective ultrasonic waves are modulated, with respect to the surface of the object (200) fed with the drug (111a), and a control unit (130) controlling the amplitudes of the respective ultrasonic waves of the amplitude-modulated ultrasonic wave group oscillated from the ultrasonic oscillating unit (120) based on a drift velocity of the drug (111a) with respect to the object (200). Accordingly, when a drug is injected into a surface of an object such as a human body using ultrasonic waves, an effective injection according to the drug can be realized.

8 Claims, 7 Drawing Sheets

U.S. PATENT DOCUMENTS

| | | | |
|---|---|---|---|
| 5,279,543 A * | 1/1994 | Glikfeld et al. | 604/20 |
| 5,445,611 A * | 8/1995 | Eppstein et al. | 604/501 |
| 5,569,844 A * | 10/1996 | Sowerby | 73/61.75 |
| 5,618,516 A | 4/1997 | Clavenna et al. | |
| 5,656,016 A | 8/1997 | Ogden | |
| 5,771,890 A * | 6/1998 | Tamada | 600/347 |
| 5,885,211 A | 3/1999 | Eppstein et al. | |
| 5,895,362 A * | 4/1999 | Elstrom et al. | 600/573 |
| 6,333,485 B1 * | 12/2001 | Haight et al. | 219/121.68 |
| 6,527,716 B1 * | 3/2003 | Eppstein | 600/309 |
| 6,652,473 B2 * | 11/2003 | Kaufman et al. | 601/1 |
| 6,853,858 B2 * | 2/2005 | Shalev | 607/3 |
| 7,556,621 B2 * | 7/2009 | Palanker et al. | 604/298 |
| 2003/0065305 A1 * | 4/2003 | Higuchi et al. | 604/501 |
| 2004/0204700 A1 * | 10/2004 | Weaver et al. | 604/500 |
| 2005/0043654 A1 | 2/2005 | Matsumura et al. | |
| 2005/0075598 A1 | 4/2005 | Redding, Jr. | |
| 2006/0264805 A1 * | 11/2006 | Singh et al. | 604/20 |
| 2007/0213645 A1 * | 9/2007 | Zumeris et al. | 601/46 |

FOREIGN PATENT DOCUMENTS

| | | |
|---|---|---|
| JP | 4-295362 A | 10/1992 |
| JP | 5-078241 A | 3/1993 |
| JP | 11-511360 A | 10/1999 |
| JP | 2004-249025 | 9/2004 |
| JP | 2006-518640 A | 8/2006 |
| WO | WO 2003/061753 A1 | 7/2003 |

* cited by examiner

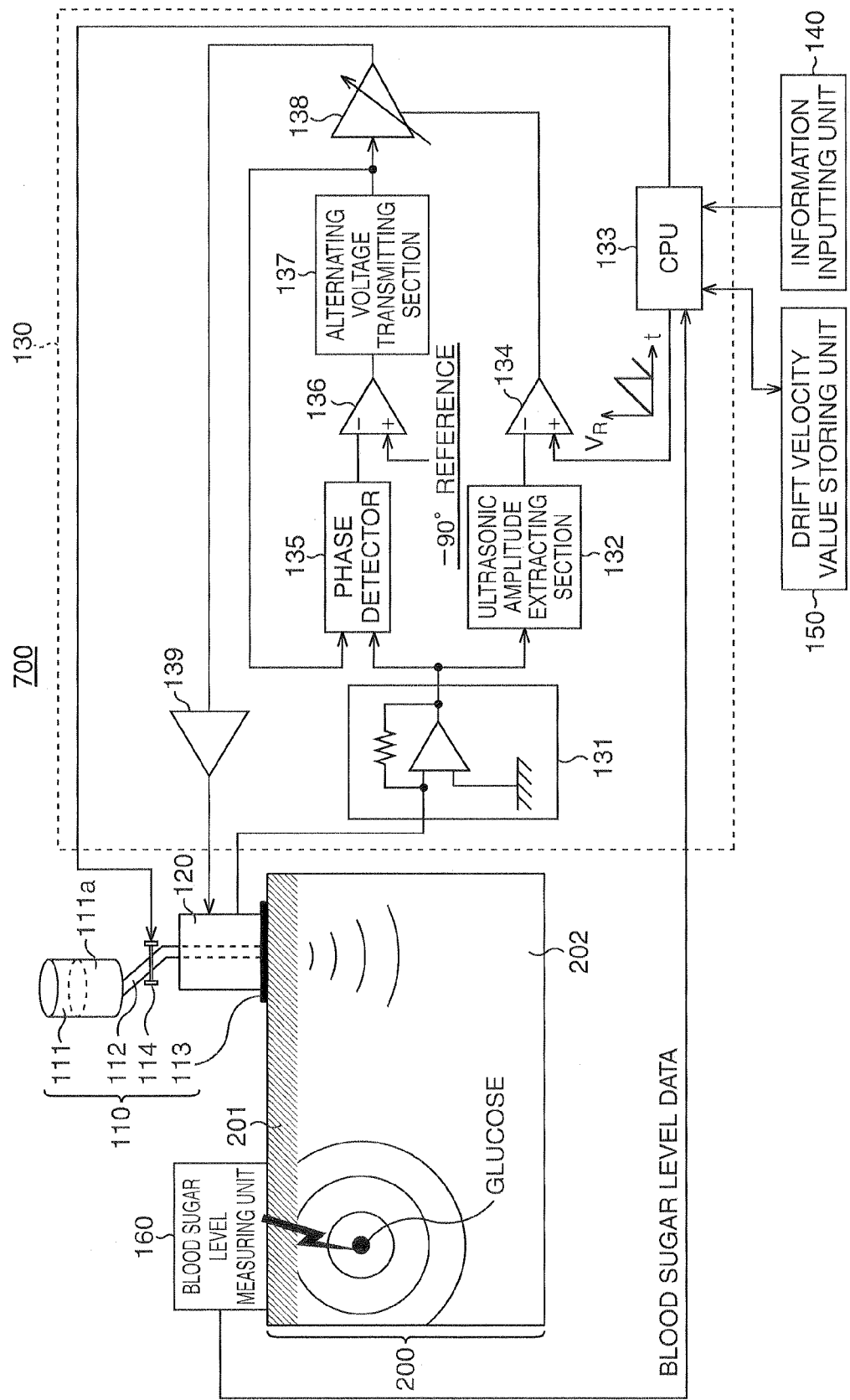

DRUG INJECTING DEVICE

CROSS-REFERENCE TO RELATED APPLICATION

This application is a National Stage entry of International Application No. PCT/JP2007/071954, having an international filing date of Nov. 13, 2007; which claims priority to Japanese Application No.: 2006-308270, filed Nov. 14, 2006, the disclosure of each of which is hereby incorporated in its entirety by reference.

TECHNICAL FIELD

The present invention relates to a drug injecting device that injects a drug fed to a surface of an object such as a human body, into a body of the object using ultrasonic vibration.

BACKGROUND ART

For example, according to the WHO (World Health Organization), there are about one hundred thirty million diabetic patients in the world as of the year 2005 in which about 10% of the patients are type I diabetic patients and confined to bed, and a portable artificial pancreas has been required to help them return to society. Further, as a technology regarding the portable artificial pancreas, a technology for injecting insulin being a drug into the blood is required, for instance.

Presently, as a route of administration of drugs, an oral, injective, noninvasive route or the like can be cited. Among the above, the injective route is the only route for directly conducting the administration into a blood vessel, and thus has been widely used. Further, as the noninvasive route, one realized by a percutaneous penetration using ultrasonic waves has been devised (refer to Patent Document 1).

Patent Document 1: International Publication Pamphlet of WO 2003/061753
Patent Document 2: Japanese Patent Application Laid-Open No. 2004-249025

SUMMARY OF THE INVENTION

For instance, in the aforementioned Patent Document 1, for making a drug penetrate through a skin, a frequency-modulated ultrasonic wave in which a frequency is modulated within a region of several MHz is applied to a surface of the skin. Here, it is considered that the injection effect becomes high as the ultrasonic wave of higher frequency is used.

However, in this case, it has not been considered at all, when a drug is injected into a surface of an object such as a human body, regarding an effective injection according to the drug. Accordingly, there is a problem, in a conventional drug injecting device using ultrasonic waves, that it is difficult to perform the effective injection according to a drug to be injected. Concretely, in the technology disclosed in Patent Document 1, it was impossible to effectively inject insulin into the aforementioned type I diabetic patients. Further, in the technology disclosed in Patent Document 1, there is a limit in penetration depth of ultrasonic wave in which it becomes shallow as the ultrasonic wave of higher frequency is used.

The present invention has been made in view of the aforementioned problems, and an object thereof is to provide a drug injecting device that realizes, when a drug is injected into a surface of an object such as a human body using ultrasonic waves, an effective injection according to the drug.

In order to solve the aforementioned problems, a drug injecting device according to the present invention has: a drug feeding unit feeding a drug to a surface of an object; an ultrasonic oscillating unit oscillating an amplitude-modulated ultrasonic wave group in which amplitudes of respective ultrasonic waves are modulated, with respect to the surface of the object fed with the drug; and a control unit controlling the amplitudes of the respective ultrasonic waves of the amplitude-modulated ultrasonic wave group based on a drift velocity of the drug with respect to the object.

According to the present invention, it becomes possible to realize, when a drug is injected into a surface of an object such as a human body using ultrasonic waves, an effective injection according to the drug.

BRIEF DESCRIPTION OF THE DRAWINGS

FIG. 7 is a block diagram showing a schematic configuration of a drug injecting device according to a second embodiment of the present invention.

DETAILED DESCRIPTION OF THE PREFERRED EMBODIMENTS

First Embodiment

Figure 1:
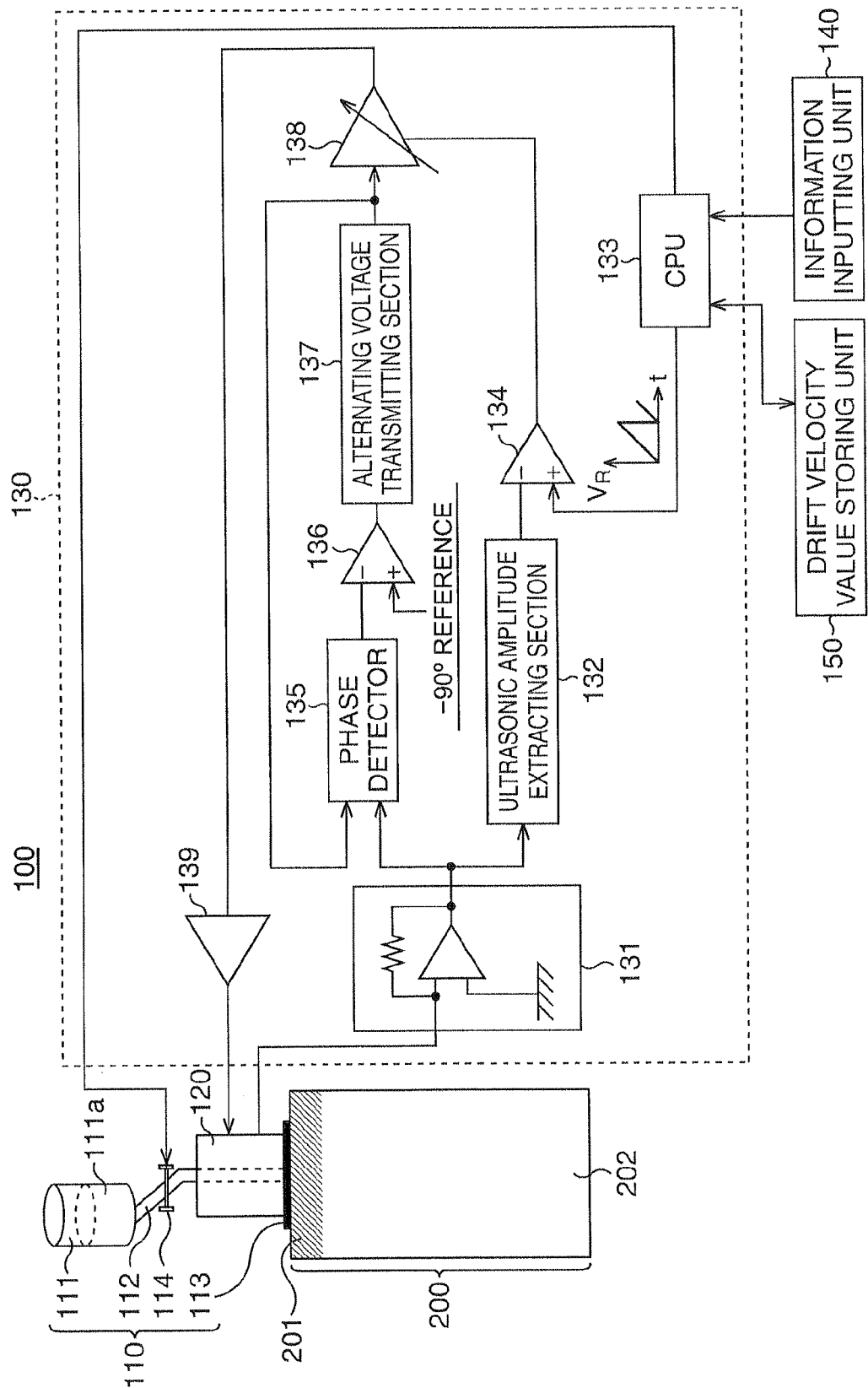
FIG. 1 is a block diagram showing a schematic configuration of a drug injecting device according to a first embodiment of the present invention.

FIG. 1 is a block diagram showing a schematic configuration of a drug injecting device 100 according to a first embodiment of the present invention.

As shown in FIG. 1, the drug injecting device 100 is configured by including a drug feeding unit 110, an ultrasonic oscillating unit 120, a control unit 130, an information inputting unit 140 and a drift velocity value storing unit 150.

The drug feeding unit 110 feeds a drug to a surface (skin 201) of an object (a human body, for instance, in the present embodiment) 200. The drug feeding unit 110 is configured by including a storage section 111 storing a drug (liquid drug, in the present embodiment) 111a, a drug-retaining buffer material 113 disposed on the surface of the object 200, a drug injecting tube 112 for introducing the drug 111a stored in the storage section 111 into the drug-retaining buffer material 113, and a valve 114 provided to the drug injecting tube 112 and adjusting an injection amount of the drug 111a to be fed to the drug-retaining buffer material 113. Further, the valve 114 is controlled by a CPU 133 of the control unit 130.

The ultrasonic oscillating unit 120 is configured by including, for instance, a piezoelectric element such as a PZT (not shown), and oscillates an amplitude-modulated ultrasonic wave group in which amplitudes of respective ultrasonic waves are modulated, with respect to the surface (skin 201) of the object 200 to which the drug 111a is fed through the drug-retaining buffer material 113. When the amplitude-modulated ultrasonic wave group is oscillated by the ultrasonic oscillating unit 120, the drug 111a retained by the drug-retaining buffer material 113 is injected into a body 202 of the object 200 through the skin 201.

The information inputting unit 140 inputs various pieces of information including information regarding a type of the drug 111a to be used and information regarding the injection amount of the drug, for instance, into the CPU 133 of the control unit 130.

The drift velocity value storing unit 150 stores a plurality of values of drift velocity, and it stores, for instance, values of drift velocity for each type of the drug 111a.

The control unit 130 controls, based on the drift velocity of the drug 111a with respect to the object 200, the amplitudes of the respective ultrasonic waves of the amplitude-modulated ultrasonic wave group oscillated from the ultrasonic oscillating unit 120. The control unit 130 is configured by including an oscillated ultrasonic wave detecting section 131, an ultrasonic amplitude extracting section 132, the CPU 133, an ultrasonic amplitude adjusting section 134, a phase detector 135, a resonant frequency adjusting section 136, an alternating voltage transmitting section 137, a voltage control amplifier 138 and a power amplifier 139.

The oscillated ultrasonic wave detecting section 131 detects the respective ultrasonic waves of the amplitude-modulated ultrasonic wave group oscillated from the ultrasonic oscillating unit 120 as voltage values. The ultrasonic amplitude extracting section 132 extracts the amplitudes of the respective ultrasonic waves detected by the oscillated ultrasonic wave detecting section 131 as voltage values.

The CPU 133 comprehensively controls an operation in the drug injecting device 100. For example, the CPU 133 extracts the corresponding value of the drift velocity from the drift velocity value storing unit 150 in accordance with the type of the drug 111a input from the information inputting unit 140, and transmits, based on the extracted value of the drift velocity, a control signal for controlling the amplitude of the amplitude-modulated ultrasonic wave group oscillated from the ultrasonic oscillating unit 120 to the ultrasonic amplitude adjusting section 134. Further, for instance, the CPU 133 controls, based on the information regarding the injection amount of the drug 111a input from the information inputting unit 140, the amount of drug 111a to be fed to the drug-retaining buffer material 113 from the storage section 111, via the valve 114, and determines the number of the respective ultrasonic waves oscillated from the ultrasonic oscillating unit 120 as one amplitude-modulated ultrasonic wave group to transmit a control signal based on the determination to the ultrasonic amplitude adjusting section 134.

Concretely, the CPU 133 outputs the control signal for controlling the amplitude of the amplitude-modulated ultrasonic wave group and the control signal regarding the number of the respective ultrasonic waves oscillated as the amplitude-modulated ultrasonic wave group, as saw-tooth signal voltages shown in FIG. 1. Here, a gradient (inclination) of a monotonically increasing part of the saw-tooth corresponds to the extracted value of the drift velocity, and the number of the respective ultrasonic waves oscillated as one amplitude-modulated ultrasonic wave group is controlled by an ON time of the saw-tooth.

The ultrasonic amplitude adjusting section 134 inputs the voltage values relating to the amplitudes of the respective ultrasonic waves extracted by the ultrasonic amplitude extracting section 132 and the saw-tooth signal voltages from the CPU 133, controls so that the amplitudes of the respective ultrasonic waves of the amplitude-modulated ultrasonic wave group oscillated from the ultrasonic oscillating unit 120 becomes equal to or less than the drift velocity, and outputs a control voltage that adjusts the number of the respective ultrasonic waves oscillated as the amplitude-modulated ultrasonic wave group.

The phase detector 135 detects a phase between a waveform of each ultrasonic wave of the amplitude-modulated ultrasonic wave group detected by the oscillated ultrasonic wave detecting section 131 and a waveform of the alternating voltage output from the alternating voltage transmitting section 137. The resonant frequency adjusting section 136 controls a phase of the alternating voltage output from the alternating voltage transmitting section 137 based on the phase detected by the phase detector 135 to thereby adjust so that the ultrasonic oscillating unit 120 turns into a resonance state. Namely, the phase detector 135 and the resonant frequency adjusting section 136 compose "a setting section" of the present invention which sets the ultrasonic oscillating unit 120 to be in the resonance state by controlling the phase of the respective ultrasonic waves of the amplitude-modulated ultrasonic wave group based on the respective ultrasonic waves of the amplitude-modulated ultrasonic wave group detected by the oscillated ultrasonic wave detecting section 131.

The alternating voltage transmitting section 137 transmits an alternating voltage (sinusoidal voltage, for instance). The voltage control amplifier 138 performs control such as modulating the alternating voltage transmitted from the alternating voltage transmitting section 137 based on the control voltage output from the ultrasonic amplitude adjusting section 134. The power amplifier 139 power-amplifies the alternating voltage modulated by the voltage control amplifier 138 and outputs it to the ultrasonic oscillating unit 120.

In the ultrasonic oscillating unit 120, the alternating voltage input from the power amplifier 139 is supplied to the aforementioned piezoelectric element (not shown), resulting that a strain based on the alternating voltage occurs in the piezoelectric element. Accordingly, the amplitude-modulated ultrasonic wave group in which the amplitudes of the respective ultrasonic waves are modulated is oscillated from the ultrasonic oscillating unit 120.

Next, a drug injecting method according to the present invention in which a drift velocity of the drug 111a with respect to the object 200 (hereinafter, the drift velocity is referred to as $V_d$) is taken into consideration will be described.

Figure 2:
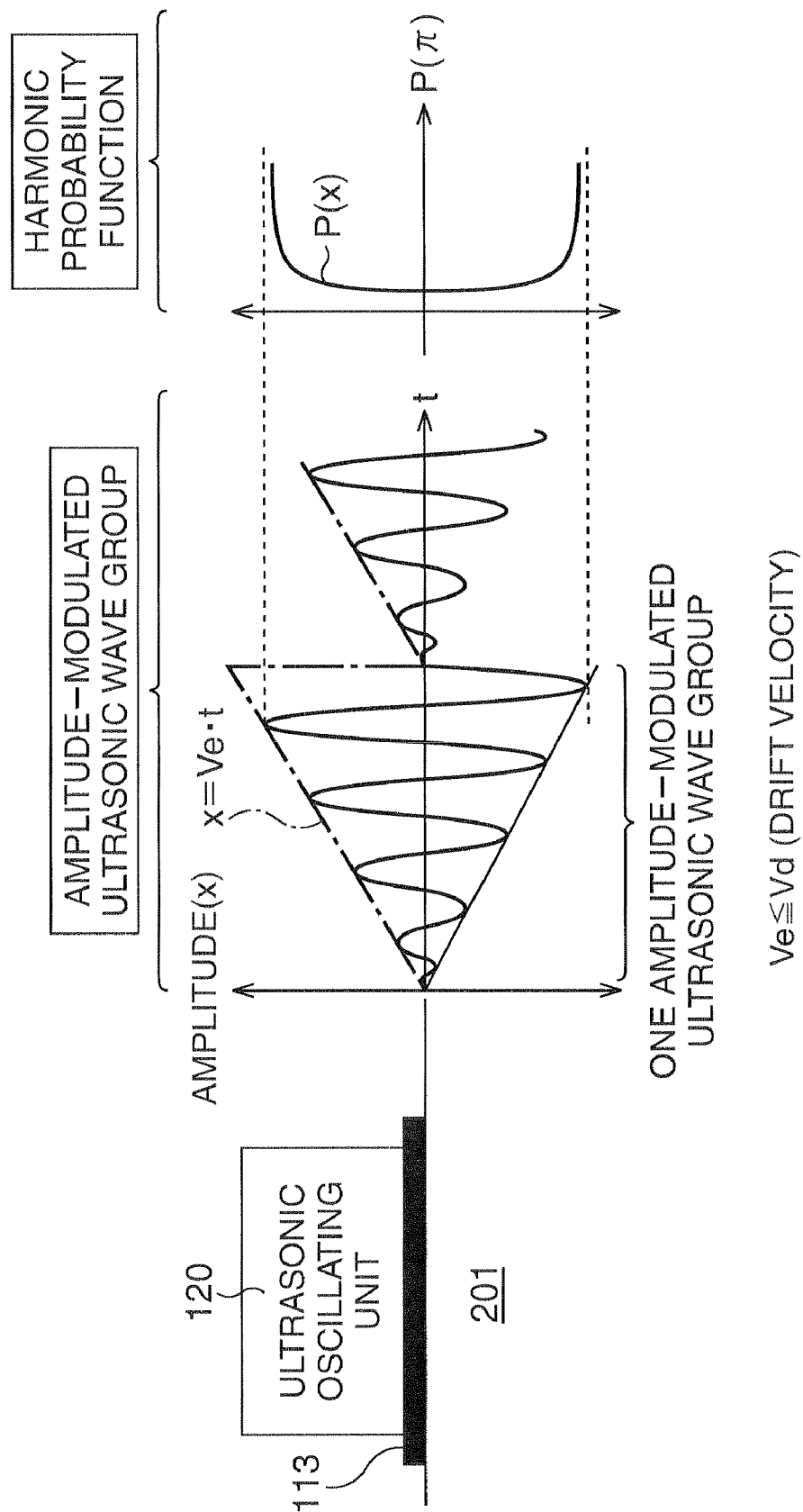
FIG. 2 is a schematic view showing an amplitude-modulated ultrasonic wave group oscillated from an ultrasonic oscillating unit with respect to a skin of an object and a harmonic probability function thereof.

FIG. 2 is a schematic view showing an amplitude-modulated ultrasonic wave group oscillated from the ultrasonic oscillating unit 120 with respect to the skin 201 of the object 200 and a harmonic probability function thereof.

First, the amplitude-modulated ultrasonic wave group shown in FIG. 2 will be described.

As shown in FIG. 2, in one amplitude-modulated ultrasonic wave group oscillated from the ultrasonic oscillating unit 120 to a surface (skin 201) of the object 200, a plurality of ultrasonic waves whose amplitudes are respectively modulated are included. The number of ultrasonic waves oscillated as the one amplitude-modulated ultrasonic wave group is determined in the control unit 130 (CPU 133) based on, for example, the information regarding the injection amount of the drug 111*a* input (set) from the information inputting unit 140.

Further, as shown in FIG. 2, the control unit 130 controls the amplitudes of the respective ultrasonic waves so that a gradient $V_e$ of the amplitudes of the respective ultrasonic waves of the amplitude-modulated ultrasonic wave group with respect to an elapsed time (t) from an oscillation starting time of one amplitude-modulated ultrasonic wave group (the gradient can also be referred to as a velocity in the amplitude of each of the ultrasonic waves with respect to the elapsed time (t)) becomes equal to or less than the drift velocity $V_d$. Here, a gradient (inclination) of a dashed and dotted line segment joining the amplitudes of the respective ultrasonic waves is represented by $V_e$ in FIG. 2.

Further, as shown in FIG. 2, the control unit 130 performs control so that the amplitudes of the respective ultrasonic waves of the one amplitude-modulated ultrasonic wave group are monotonically increased from a first ultrasonic wave at the time of starting the oscillation of the amplitude-modulated ultrasonic wave group to a last ultrasonic wave relating to the number of ultrasonic waves to be oscillated which is determined based on the information regarding the injection amount of the drug 111*a*. Namely, the amplitudes of the respective ultrasonic waves are monotonically increased with the gradient $V_e$.

Besides, as shown in FIG. 2, after performing the control regarding the last ultrasonic wave of the one amplitude-modulated ultrasonic wave group, the control unit 130 performs control for making the ultrasonic oscillating unit 120 oscillate a next amplitude-modulated ultrasonic wave group, and controls so that a shape of the oscillated amplitude-modulated ultrasonic wave group takes a saw-tooth shape shown by a dashed and dotted line in FIG. 2.

Subsequently, a general principle regarding the harmonic probability function shown in FIG. 2 will be explained.

If a concentration is set as C, a flow velocity J occurred in a homogenous system (solid body) by power F is represented by the following expression (1) and expression (2).

[Formula 1]

$$J = -D\nabla C - D\frac{CF}{KT} \quad (1)$$

$$= J_C + J_F \quad (2)$$

D: diffusion coefficient, K: Boltzmann factor,
T: absolute temperature, $J_C$: flow caused by concentration gradient,
$J_F$: flow caused by vibrating stress Further, the drift velocity $V_d$ of the drug 111*a* with respect to the object 200 is represented by the following expression (3).

[Formula 2]

$$V_d = \frac{D}{KT}F \quad (3)$$

Here, as shown in the following expression (4), if it is set that the injection with the use of the vibrating stress is available and an amplitude of the vibrating stress is A, the amplitude A of the vibrating stress is represented by the following expression (5).

[Formula 3]

$$J_C << J_F \quad (4)$$

$$A = E\epsilon \cos \omega \quad (5)$$

Here, E and $\epsilon$ in the expression (5) respectively represent Young's modulus and a strain amplitude. Further, if a velocity of the strain amplitude $\epsilon$ is set as v, a wave front x of the strain amplitude $\epsilon$ and a presence time $\Delta t$ of $x+\Delta x$ are represented by the following expression (6) and expression (7).

[Formula 4]

$$\Delta t = 2\left|\frac{\Delta x}{V}\right| = \left|\frac{2\Delta x}{\omega \epsilon \sin \omega t}\right| \quad (6)$$

$$= \frac{2\Delta x}{\omega \sqrt{\epsilon^2 - x^2}} \quad (7)$$

Further, if a vibration period is set as $\tau$, a presence probability P(x) of the wave front x of the strain amplitude $\epsilon$ is represented by the following expression (8).

[Formula 5]

$$P(x) = \frac{2\Delta x}{\tau \omega \sqrt{\epsilon^2 - x^2}} \quad (8)$$

The presence probability P(x) represented by the expression (8) corresponds to a characteristic of the harmonic probability function shown in FIG. 2.

Meanwhile, a jumping frequency $\omega_j$ of a diffusion material provides the drift velocity $V_d$. When an external force frequency $\omega_F$ meets a condition represented by the following expression (9), it is not possible to follow the external force, resulting that a point of an external pressure amplitude $P(x)_{MAX}$ operates as a drift velocity operational power point.

[Formula 6]

$$\omega_j << \omega_F \quad (9)$$

A case is considered in which a PZT is used as a piezoelectric element of the ultrasonic oscillating unit 120 and the PZT is set as a driving vibration source for injecting the drug 111*a*. An acoustic impedance of PZT is about $34.8 \times 10^6$ kg/m²·s, and an acoustic impedance of muscle is about $1.5 \times 10^6$ kg/m²·s, in which a magnitude of the acoustic impedance of muscle is about one-twentieth of that of the acoustic impedance of PZT.

In addition, it is confirmed according to an experiment that an attenuation coefficient of acoustic vibration of human body is about 0.15/cm under an ultrasonic vibration frequency of 80 kHz, so that a human body is regarded as a relaxation system. Meanwhile, a vibration amplitude applied to the human body (object 200) by the piezoelectric element of the ultrasonic oscillating unit 120 appears only on the positive side of an amplitude pressure function of a sinusoidal wave (sin wave). Namely, only an amplitude on the positive side of the sin wave is applied to the human body (object 200) as impact force. An equivalent circuit diagram of the dynamic model is shown in FIG. 3.

Figure 3:
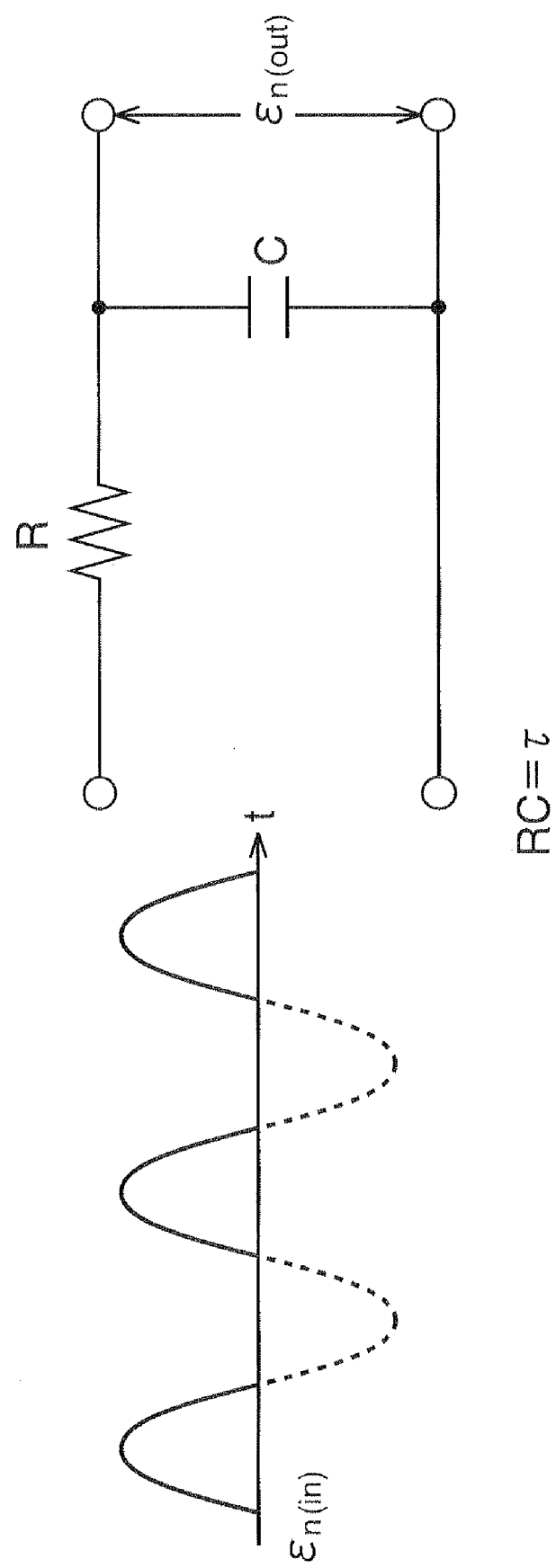
FIG. 3 is an equivalent circuit diagram of a dynamic model in a strain positive amplitude of sin wave.

A strain positive amplitude A(t) of the sin wave shown in FIG. 3 is represented by the following expression (10).

[Formula 7]

$$A(t)=|\epsilon \sin \omega t|+\epsilon \sin \omega t \quad (10)$$

When the expression is expanded into Fourier series, the strain positive amplitude A(t) is represented by the following expression (11).

[Formula 8]

$$A(t) = \frac{\varepsilon_0}{2} + \sum_{n=1}^{\infty} \varepsilon_n \cos 2n\omega t \quad (11)$$

Here, $\epsilon_0$ in the expression (11) is represented by the following expression (12), and $\epsilon_n$ in the expression (11) is represented by the following expression (13).

[Formula 9]

$$\varepsilon_0 = \frac{4\varepsilon}{\pi} \quad (12)$$

$$\varepsilon_n = \frac{4\varepsilon}{\pi(1-4n^2)} \quad (13)$$

When the amplitude $\epsilon_n$ shown in the expression (13) is input into the relaxation system shown in FIG. 3, it becomes a product of a relaxation function, resulting that $\epsilon_{n(out)}$ is represented by the following expression (14).

[Formula 10]

$$\varepsilon_{n(out)} = \frac{1}{1+(\omega\tau)^2} \frac{4\varepsilon}{\pi(1-4n^2)} \quad (14)$$

The expression (14) indicates that a contribution with respect to the drift velocity $V_d$ as a vibration term becomes effective as a driving frequency is lowered. Here, the expression (12) represents a static pressure amplitude which does not depend on an ultrasonic driving frequency ω. Further, if the amplitude modulation is performed so that the amplitude takes a saw-tooth shape as in the amplitude-modulated ultrasonic wave group shown in FIG. 2, the expression (12) is represented by the following expression (15).

[Formula 11]

$$\varepsilon_0 = \frac{4}{\pi} V_e t \quad (15)$$

Here, as described above, $V_e$ indicates the velocity in the amplitude of each of the ultrasonic waves of the amplitude-modulated ultrasonic wave group with respect to the elapsed time (t) from the oscillation starting time of the one amplitude-modulated ultrasonic wave group, namely, the inclination (gradient) of the amplitude-modulated ultrasonic wave group in a saw-tooth shape shown by a dashed and dotted line in FIG. 2, and an injection condition of the drug 111a has to satisfy the following expression (16) as described above.

[Formula 12]

$$V_e \leq V_d \quad (16)$$

Next, an experimental result using the drug injecting device 100 according to the first embodiment of the present invention will be explained.

In the experiment, a transparent gelatin is used as the object 200, and a filter paper is used as the drug-retaining buffer material 113. In the filter paper, a food red dye dissolved in glycerol, which corresponds to the drug 111a, is infiltrated. Subsequently, the filter paper in which the food red dye is infiltrated is placed on the transparent gelatin which corresponds to the object 200, and ultrasonic waves are oscillated by an ultrasonic oscillating unit from the above of the filter paper. An oscillation frequency of the ultrasonic waves at this time is set as 80 kHz.

Figure 4:
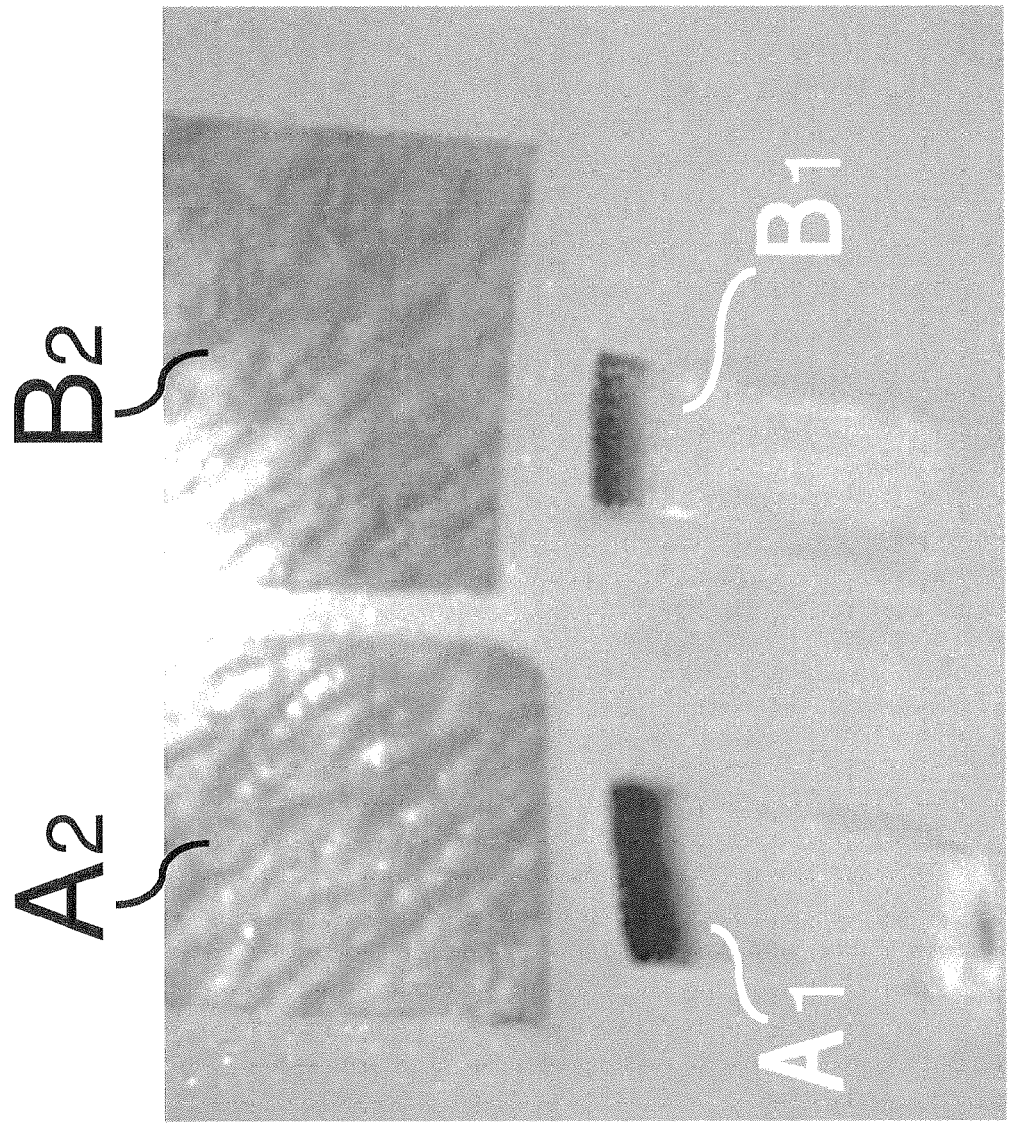
FIG. 4 illustrates a comparative example and is a picture showing a state in which a drug (food red dye dissolved in glycerol) is diffused at the time of oscillating ultrasonic waves having fixed amplitudes from an ultrasonic oscillating unit of a drug injecting device.

FIG. 4 illustrates a comparative example and is a picture showing a state in which a drug (food red dye dissolved in glycerol) is diffused at the time of oscillating ultrasonic waves having fixed amplitudes from an ultrasonic oscillating unit of a drug injecting device.

$A_1$ and $A_2$ shown in FIG. 4 are a gelatin and a filter paper, respectively, when the ultrasonic waves having fixed amplitudes are oscillated for 30 minutes from the ultrasonic oscillating unit. Further, for reference, $B_1$ and $B_2$ shown in FIG. 4 indicate a gelatin and a filter paper when diffusion through a concentration gradient is performed for 30 minutes without conducting the oscillation of ultrasonic waves from the ultrasonic oscillating unit. Colored parts of the respective gelatins $A_1$ and $B_1$ respectively indicate the food red dye injected through each of the filter papers $A_2$ and $B_2$.

Figure 5:
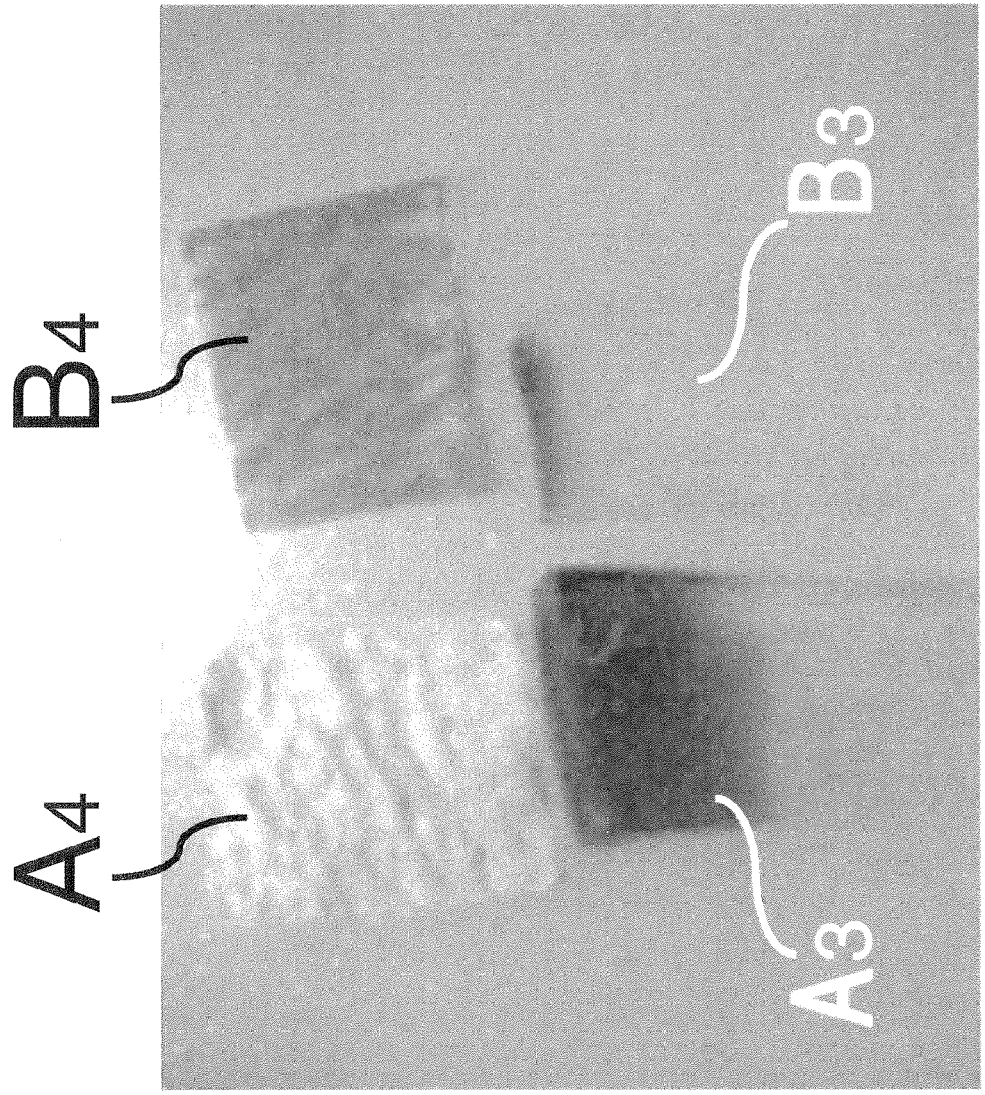
FIG. 5 is a picture showing a state in which a drug (food red dye dissolved in glycerol) is diffused at the time of oscillating an amplitude-modulated ultrasonic wave group from an ultrasonic oscillating unit of the drug injecting device according to the first embodiment of the present invention.

FIG. 5 is a picture showing a state in which a drug (food red dye dissolved in glycerol) is diffused at the time of oscillating an amplitude-modulated ultrasonic wave group from the ultrasonic oscillating unit 120 of the drug injecting device 100 according to the first embodiment of the present invention.

$A_3$ and $A_4$ shown in FIG. 5 are a gelatin and a filter paper, respectively, when the amplitude-modulated ultrasonic wave group shown in FIG. 2 is oscillated for 30 minutes from the ultrasonic oscillating unit 120. Here, in the experiment shown by $A_3$ and $A_4$, in order to detect the drift velocity ($V_d$) of the gelatin $A_3$, oscillation is performed under a 60 second period of oscillation time for one amplitude-modulated ultrasonic wave group. Further, for reference, $B_3$ and $B_4$ shown in FIG. 5 indicate a gelatin and a filter paper when diffusion through a concentration gradient is performed for 30 minutes without conducting the oscillation of ultrasonic waves from the ultrasonic oscillating unit 120. Colored parts of the respective gelatins $A_3$ and $B_3$ respectively indicate the food red dye injected through each of the filter papers $A_4$ and $B_4$.

As shown by the gelatin $A_1$ in FIG. 4, in a drug injecting method according to the comparative example in which the ultrasonic waves with fixed amplitudes are oscillated, the injection amount of the food red dye does not make much difference compared to that in the gelatin $B_1$ in which only the diffusion through the concentration gradient is performed. Meanwhile, as shown by the gelatin $A_3$ in FIG. 5, in the drug injecting method according to the present embodiment in which the amplitude-modulated ultrasonic wave group is oscillated, the injection amount of the food red dye is significantly increased compared to that in the gelatin $B_3$ in which only the diffusion through the concentration gradient is performed. In this case, a large amount of food red dye is injected into the gelatin $A_3$ from the filter paper $A_4$, so that the amount of coloring on the filter paper $A_4$ made by the food red dye is decreased.

Specifically, if considered based on the injection amount of the food red dye injected into the gelatin $A_1$ in FIG. 4 and the injection amount of the food red dye injected into the gelatin $A_3$ in FIG. 5, it can be proved that the injection can be realized more effectively when the amplitude-modulated ultrasonic wave group is supplied by considering the drift velocity ($V_d$) than when the ultrasonic waves having fixed amplitudes are kept supplied.

Next, an experimental result of a diffusive concentration of each type of the drug 111a with respect to the object 200 when the frequency of the amplitude-modulated ultrasonic wave group (saw-tooth wave having a saw-tooth shape) shown in FIG. 2 is set as a parameter will be explained.

Figure 6:
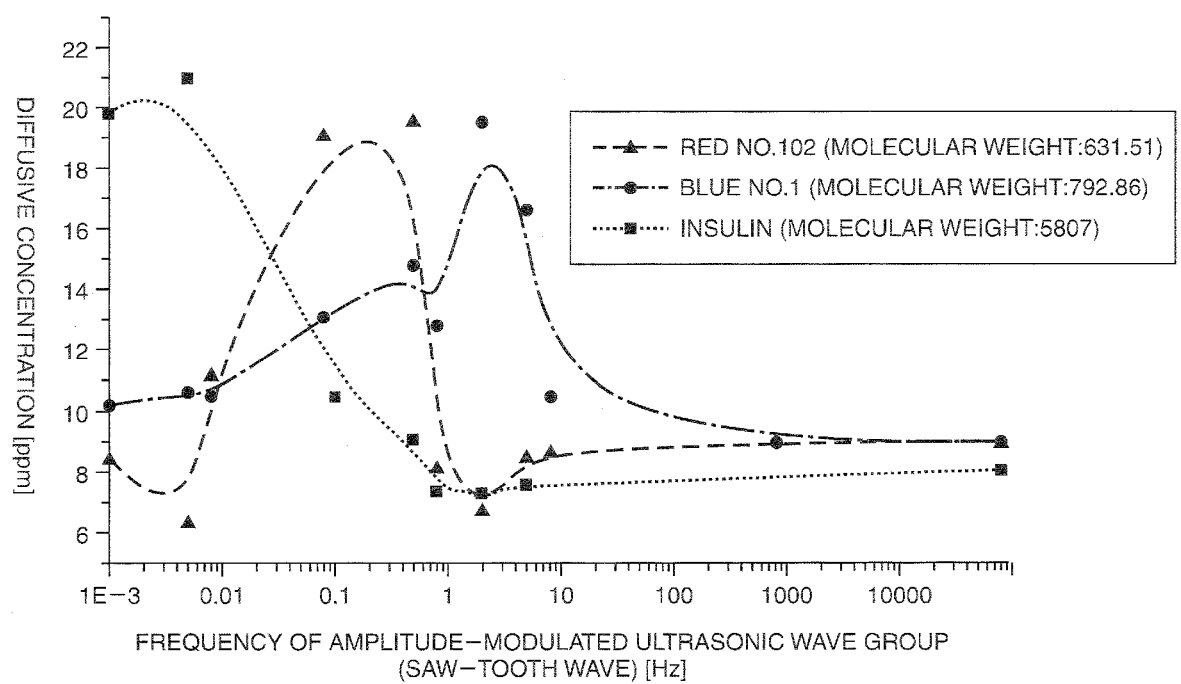
FIG. 6 is a characteristic diagram showing a diffusive concentration in which respective drugs are diffused in an object (concretely, 20 cc of pure water through a pig bladder membrane with a thickness of 1 mm) at the time of oscillating the amplitude-modulated ultrasonic wave group from the ultrasonic oscillating unit of the drug injecting device according to the first embodiment of the present invention.

FIG. 6 is a characteristic diagram showing diffusive concentrations in which respective drugs are diffused in an object (concretely, 20 cc of pure water through a pig bladder membrane with a thickness of 1 mm) when the amplitude-modulated ultrasonic wave group is oscillated from the ultrasonic oscillating unit of the drug injecting device according to the first embodiment of the present invention.

In the experiment shown in FIG. 6, characteristics are shown in which three types of Red No. 102 (CI name (English name): Acid Red 18) whose molecular weight is 631.51, Blue No. 1 (CI name (English name): Food Blue 2) whose molecular weight is 792.86, and insulin whose molecular weight is 5807 are used as the drugs 111a. Further, a horizontal axis in FIG. 6 indicates the frequency of the amplitude-modulated ultrasonic wave group shown in FIG. 2, and a vertical axis in FIG. 6 indicates the diffusive concentration of each of the above-described drugs 111a with respect to the object 200.

As shown in FIG. 6, the insulin has the lowest frequency domain of the amplitude-modulated ultrasonic wave group, among the three types of drugs 111a, in which the diffusive concentration with respect to the object 200 reaches a peak. The molecular weight of the insulin is nearly ten times the molecular weight of the Blue No. 1 and that of the Red No. 102, and this matches a physical theoretical prediction of "one with a large amount of molecular weight is difficult to be diffused".

As described above, it is confirmed that the frequency domain of the amplitude-modulated ultrasonic wave group in which the diffusive concentration with respect to the object 200 reaches the peak is also changed in accordance with the type of the drug 111a.

According to the first embodiment of the present invention, since it is designed to control the amplitudes of the respective ultrasonic waves of the amplitude-modulated ultrasonic wave group oscillated from the ultrasonic oscillating unit 120 based on the drift velocity $V_d$ of the drug 111a with respect to the object 200, when a drug is injected into a surface of an object such as a human body using ultrasonic waves, it becomes possible to realize an effective injection according to the drug.

Note that in the present embodiment, the control unit 130 is designed to perform control regarding the amplitudes of the respective ultrasonic waves of the amplitude-modulated ultrasonic wave group oscillated from the ultrasonic oscillating unit 120 and regarding the number of the respective ultrasonic waves oscillated as one amplitude-modulated ultrasonic wave group based on the information relating to the drug 111a input from the information inputting unit 140. However, the present invention is not limited to this and, for example, it may take an embodiment in which not only the information relating to the drug 111a shown in the present embodiment but also information relating to the measured acoustic impedance of the object 200 is input from the information inputting unit 140 to thereby add the information relating to the acoustic impedance in addition to the information relating to the drug 111a, and the control regarding the amplitudes of the respective ultrasonic waves of the amplitude-modulated ultrasonic wave group oscillated from the ultrasonic oscillating unit 120 and the control regarding the number of the respective ultrasonic waves oscillated as one amplitude-modulated ultrasonic wave group are performed.

Second Embodiment

FIG. 7 is a block diagram showing a schematic configuration of a drug injecting device 700 according to a second embodiment of the present invention.

As shown in FIG. 7, the drug injecting device 700 according to the second embodiment corresponds to the drug injecting device 100 according to the first embodiment shown in FIG. 1 to which a blood sugar level measuring unit 160 is further provided. Further, in the second embodiment, insulin is used as the drug 111a.

The blood sugar level measuring unit 160 measures a blood sugar level indicating a concentration of glucose (grape sugar) in the blood in the body 202 of the object 200. For instance, the blood sugar level measuring unit 160 is composed of a device shown in FIG. 1 of Patent Document 2.

In the second embodiment, the CPU 133 performs control for making the ultrasonic oscillating unit 120 oscillate the amplitude-modulated ultrasonic wave group when information relating to the blood sugar level measured by the blood sugar level measuring unit 160 (blood sugar level data) becomes equal to or more than a threshold value, in addition to the control in the first embodiment. At this time, the CPU 133 performs control for driving the valve 114 to feed the drug 111a from the storage section 111 to the object 200, for instance. This is because, when the insulin being the drug 111a is injected into the object 200, the blood sugar level of the object 200 is lowered.

Meanwhile, when the information relating to the blood sugar level measured by the blood sugar level measuring unit 160 (blood sugar level data) becomes less than the threshold value, the CPU 133 performs control for making the ultrasonic oscillating unit 120 stop the oscillation of the amplitude-modulated ultrasonic wave group. At this time, the CPU 133 performs control for driving the valve 114 to stop the feeding of the drug 111a from the storage section 111 to the object 200, for instance.

Further, in the CPU 133, information regarding the threshold value which is compared to the information relating to the blood sugar level (blood sugar level data) is input from, for instance, the information inputting unit 140. For example, in the present embodiment, a value of 130 mg/dl is input from the information inputting unit 140 as the threshold value of the blood sugar level.

According to the second embodiment of the present invention, it is designed such that the oscillation of the amplitude-modulated ultrasonic wave group from the ultrasonic oscillating unit 120 is stopped when the information relating to the blood sugar level measured by the blood sugar level measuring unit 160 (blood sugar level data) becomes less than the threshold value, so that it is possible to obtain an effect of the first embodiment, and further, it is possible to avoid the situation in which a drug (insulin) is excessively fed to an object such as a human body to which the drug is already sufficiently fed. Accordingly, it also becomes possible to secure safety of an object such as a human body.

Note that in the respective embodiments of the present invention, an explanation in which the object 200 is assumed to be a human body is made, but, the present invention is not limited to this, and it can be applied to another animal as well.

Functions of the respective means of the control unit 130 shown in FIG. 1 and FIG. 7 composing the drug injecting device according to the aforementioned respective embodiments of the present invention can be realized by operating a program stored in a RAM or ROM of a computer. The program and a computer readable storage medium recording the program are within the scope of the present invention.

Specifically, the program is recorded in, for example, the storage medium such as a CD-ROM, or provided to the computer via various transmission media. As a storage medium recording the program, a flexible disk, a hard disk, a magnetic tape, a magneto-optical disk, a nonvolatile memory card, and the like can be used in addition to the CD-ROM. Meanwhile, as a transmission medium of the program, a communication medium in a computer network (LAN, WAN such as the Internet, a wireless communication network, and the like) system to supply the program information by propagating it as a carrier wave can be utilized. Further, as a communication medium at this time, a wired circuit such as an optical fiber, a wireless circuit, or the like can be cited.

Further, the present invention is not limited to an example in which the computer executes the supplied program to realize the function of the drug injecting device according to the respective embodiments of the present invention. Also when the program collaborates with an OS (operating system), another application software, or the like, which are operating in the computer, to realize the function of the drug injecting device according to the respective embodiments of the present invention, such a program is within a scope of the present invention. Further, when all or parts of the processing of the supplied program are performed by a function expansion board or a function expansion unit of the computer to realize the function of the drug injecting device according to the respective embodiments of the present invention, such a program is within the scope of the present invention.

Further, the present embodiments are to be considered in all respects as illustrative and no restrictive, and all changes which come within the meaning and range of equivalency of the claims are therefore intended to be embraced therein. The invention may be embodied in other specific forms without departing from the spirit or essential characteristics thereof.

INDUSTRIAL APPLICABILITY

According to the present invention, it becomes possible to realize, when a drug is injected into a surface of an object such as a human body using ultrasonic waves, an effective injection according to the drug.

What is claimed is:

1. A drug injecting device, comprising:
a drug feeding unit feeding a drug to a surface of an object;
an ultrasonic oscillating unit oscillating an amplitude-modulated ultrasonic wave group in which amplitudes of respective ultrasonic waves are modulated, with respect to the surface of the object fed with the drug; and
a control unit controlling the amplitudes of the respective ultrasonic waves of the amplitude-modulated ultrasonic wave group based on a drift velocity of the drug extracted from a drift velocity storage unit with respect to the object.

2. The drug injecting device according to claim 1,
wherein said control unit controls the amplitudes of the respective ultrasonic waves so that a gradient of the amplitudes of the respective ultrasonic waves of the amplitude-modulated ultrasonic wave group with respect to an elapsed time from an oscillation starting time of the amplitude-modulated ultrasonic wave group becomes equal to or less than the drift velocity.

3. The drug injecting device according to claim 1,
wherein said control unit determines the number of the respective ultrasonic waves to be oscillated as the amplitude-modulated ultrasonic wave group in accordance with a set injection amount of the drug.

4. The drug injecting device according to claim 3,
wherein said control unit performs control so that the amplitudes of the respective ultrasonic waves of the amplitude-modulated ultrasonic wave group are monotonically increased from a first ultrasonic wave at the time of starting the oscillation of the amplitude-modulated ultrasonic wave group to a last ultrasonic wave relating to the determined number of ultrasonic waves to be oscillated.

5. The drug injecting device according to claim 4,
wherein said control unit performs, after performing the control regarding the last ultrasonic wave of the amplitude-modulated ultrasonic wave group, control for making said ultrasonic oscillating unit oscillate a next amplitude-modulated ultrasonic wave group, and controls so that a shape of the amplitude-modulated ultrasonic wave group takes a saw-tooth shape.

6. The drug injecting device according to claim 1,
wherein the storage unit storing a value of the drift velocity for each type of the drug; and
the device further comprises an information inputting unit inputting at least information relating to the type of the drug to be used,
wherein said control unit extracts a corresponding value of the drift velocity from said storage unit in accordance with the type of the drug input from said information inputting unit, and controls the amplitude of the amplitude-modulated ultrasonic wave group based on the extracted value of the drift velocity.

7. The drug injecting device according to claim 1,
wherein said control unit includes a detecting section detecting the respective ultrasonic waves of the amplitude-modulated ultrasonic wave group oscillated from said ultrasonic oscillating unit, and a setting section setting said ultrasonic oscillating unit to be in a resonance state by controlling a phase of the respective ultrasonic waves of the amplitude-modulated ultrasonic wave group based on the respective ultrasonic waves detected by the detecting section.

8. The drug injecting device according to claim 1, further comprising
a blood sugar level measuring unit measuring a blood sugar level inside the object,
wherein said control unit performs control for making said ultrasonic oscillating unit oscillate the amplitude-modulated ultrasonic wave group when the blood sugar level measured by said blood sugar level measuring unit becomes equal to or more than a threshold value, and further performs control for making said ultrasonic oscillating unit stop the oscillation of the amplitude-modulated ultrasonic wave group when the blood sugar level measured by said blood sugar level measuring unit becomes less than the threshold value.

* * * * *